US008789695B2

(12) United States Patent
Mason

(10) Patent No.: US 8,789,695 B2
(45) Date of Patent: Jul. 29, 2014

(54) CONTAINER FOR MEDICAL ACCESSORY PROCESSING

(75) Inventor: David Robert Mason, Southend-on Sea (GB)

(73) Assignee: Medicart International Limited (GB)

( * ) Notice: Subject to any disclaimer, the term of this patent is extended or adjusted under 35 U.S.C. 154(b) by 0 days.

(21) Appl. No.: 13/989,104

(22) PCT Filed: Oct. 14, 2011

(86) PCT No.: PCT/GB2011/052000
§ 371 (c)(1),
(2), (4) Date: May 23, 2013

(87) PCT Pub. No.: WO2012/069800
PCT Pub. Date: May 31, 2012

(65) Prior Publication Data
US 2013/0233746 A1 Sep. 12, 2013

(30) Foreign Application Priority Data
Nov. 25, 2010 (GB) .................................. 1020007.9

(51) Int. Cl.
*A61B 19/02* (2006.01)
*A61B 17/00* (2006.01)
*A61B 19/00* (2006.01)

(52) U.S. Cl.
CPC ........... *A61B 19/026* (2013.01); *A61B 19/0287* (2013.01); *A61B 2019/0209* (2013.01); *A61B 2017/0023* (2013.01); *A61B 2019/0245* (2013.01); *A61B 2019/343* (2013.01); *A61B 2019/024* (2013.01)
USPC ............................. 206/363; 220/4.21; 206/1.5

(58) Field of Classification Search
CPC ............. B65D 77/2088; B65D 43/162; A61B 19/026; A61B 19/02; D06F 95/006
USPC ................... 206/363, 370, 438, 439, 807, 1.5; 220/4.21
See application file for complete search history.

(56) References Cited

U.S. PATENT DOCUMENTS 4,658,955 A * 4/1987 Eichner .......................... 206/307
4,782,977 A * 11/1988 Watanabe et al. ............. 220/324
(Continued)

FOREIGN PATENT DOCUMENTS

DE           94181853       12/1994
DE         102009011528      8/2010
(Continued)

OTHER PUBLICATIONS

U.K. Search Report, Intellectual Property Office, 2 pages, Nov. 3, 2011.
(Continued)

*Primary Examiner* — Steven A. Reynolds
*Assistant Examiner* — King M Chu
(74) *Attorney, Agent, or Firm* — Renner Kenner Greive Bobak Taylor & Weber

(57) ABSTRACT

A container (10) is provided for housing a medical accessory (20), such as a valve of a flexible medical endoscope, during processing (cleaning and high level disinfection) thereof following its use on a patient. The container (10) has a closure mechanism (15) comprising first and second complementary members (16, 17) adapted to engage with one another. Once engaged, the first and second complementary members (16, 17) cannot be disengaged from one another without the container (10) breaking. The container (10) is thus suitable only for single use, so as to prevent cross-contamination, and to comply with appropriate public health guidelines.

17 Claims, 3 Drawing Sheets

(56) References Cited

U.S. PATENT DOCUMENTS

| | | |
|---|---|---|
| 5,163,557 A | 11/1992 | Sokolowski |
| 5,234,124 A | 8/1993 | Buckner, III et al. |
| 5,285,918 A * | 2/1994 | Weisburn et al. ............. 220/265 |
| 5,294,413 A * | 3/1994 | Riihimaki et al. ............. 422/297 |
| 5,372,787 A | 12/1994 | Ritter |
| 5,979,690 A * | 11/1999 | Hartley ........................ 220/266 |
| 2002/0162838 A1* | 11/2002 | Leaphart et al. ............. 220/4.21 |
| 2006/0289549 A1* | 12/2006 | Vovan ........................... 220/791 |
| 2007/0045317 A1* | 3/2007 | Rosender et al. ............. 220/266 |
| 2007/0138180 A1* | 6/2007 | Vovan ........................... 220/266 |
| 2007/0212277 A1* | 9/2007 | Riley ............................ 422/292 |
| 2007/0272688 A1* | 11/2007 | Longo et al. ................. 220/4.23 |
| 2008/0116095 A1* | 5/2008 | Riley et al. ................... 206/363 |
| 2010/0158751 A1 | 6/2010 | Friderich et al. |

FOREIGN PATENT DOCUMENTS

| | | |
|---|---|---|
| EP | 0307173 | 3/1989 |
| EP | 0808782 | 11/1997 |
| FR | 2543110 | 9/1984 |
| GB | 2475948 | 8/2011 |

OTHER PUBLICATIONS

International Search Report, European Patent Office, 3 pages, Feb. 16, 2012.

* cited by examiner

CONTAINER FOR MEDICAL ACCESSORY PROCESSING

This invention relates to a container for medical accessory processing. In particular, it relates to a single-use container for housing the valves of a flexible medical endoscope during processing. The term "processing" is used herein to refer to a regime of cleaning and high level disinfection of medical equipment following its use on a patient.

Following use on a patient, medical equipment must be processed to, and maintained at, a high level of disinfection. This is a particular necessity for medical equipment utilised in invasive procedures, such as flexible medical endoscopes, with which the present invention is primarily concerned.

Flexible medical endoscopes typically comprise a number of auxiliary channels for the delivery of air, water or other fluids. These may be utilised for the delivery of such fluids to the interior of a patient where this required during a medical procedure, for the removal of fluid (by suction) from the interior of patient, or for cleaning the viewing window or lens of the endoscope. Operation of these channels is typically controlled by a number of valves (sometimes referred to as pistons) operated remotely by the practitioner carrying out the endoscopy procedure.

During processing of the flexible medical endoscope following its use on a patient, the valves must be removed, in order that each of the auxiliary channels can be thoroughly cleaned and disinfected. The valves themselves must also be subjected to the same processing regime to bring them to a state of high level disinfection. Typically, processing of flexible medical endoscopes and associated accessories such as the valves, is now carried out on an automated basis using a specially designed processing machine, known as an Automated Endoscope Reprocessing, or AER, machine. In a busy hospital endoscopy department this can cause problems, since the valves specific to a particular endoscope can easily become separated from that endoscope during processing. This can lead to cross-contamination if a set of valves associated with one endoscope are accidentally inserted into a different endoscope.

Accessories such as endoscope valves are often placed into auxiliary containers, before placed into the AER machine along with the endoscope. Ideally, such auxiliary containers should only be used once, and then disposed of, in order to eliminate them as a possible source of cross-contamination between different endoscopes which may be processed using the same machine. Indeed, concerns regarding the levels of disinfection to which endoscopes and their associated accessories are processed, and at which they are maintained, have led to increasingly strict guidelines regulating the manner in which processing is carried out. For example, the British Society of Gastroenterology (BSG) Guidelines for Decontamination of Equipment for Gastrointestinal Endoscopy (February 2008), now stipulate that such auxiliary containers must be single use items, and must be disposed of after use. In practice however, this ideal is not always achieved, in particular since it is often not possible to tell whether a container has been used previously.

The present invention seeks to address the above issues by providing a container for housing the valves of a flexible medical endoscope during processing, which container is capable of being used only a single time, and which provides means for ensuring that a particular set of valves remains specific to a particular endoscope. Although the container of the present invention has been developed with endoscope valves in mind, it is envisaged that the container may be adapted for use with substantially all kinds of medical accessory, and the disclosure of the invention herein should be construed accordingly.

According to the present invention there is provided a container for housing a medical accessory during processing thereof, said container having a closure mechanism adapted such that, once closed, said closure mechanism cannot be re-opened without the container breaking, thereby rendering said container suitable only for single use.

The container is preferably adapted to house a component of a flexible medical endoscope, most preferably a valve or piston, or a set of valves or pistons.

The container is also preferably adapted to be processed in a medical equipment processing machine, most preferably an AER machine.

In a preferred embodiment of the present invention, the closure mechanism comprises first and second complementary members adapted to engage with one another such that, once engaged, the first and second complementary members cannot be disengaged without breaking. Preferably, one of the first and second members comprises a latch, and the other of said members comprises a channel adapted to receive the latch.

In a further preferred variant, the latch is provided with an extending barb, and the channel is adapted to permit the ingress of the barb, but to prevent removal thereof. To achieve this, the channel may preferably comprise one or more detents adapted to engage with the barb, thereby to prevent removal of the barb from the channel. The barb may be angled relative to the latch in order to enhance this effect.

The container may desirably be formed so as to have a body portion and a lid portion, with the lid portion preferably being hingedly mounted on the body portion. Most preferably, the body portion and the lid portion are formed as, or from, a single piece of plastics material, and are connected to one another via a live hinge. Alternatively, or additionally, the lid portion may be shaped and/or adapted so as to engage with the body portion, upon closure of the container.

In embodiments of the present invention having the body-and-lid arrangement described above, one of the first and second complementary members is preferably provided on the body portion, with the other of said complementary members being provided on the lid portion.

In embodiments of the present invention having both the latch-and-channel arrangement and the body-and-lid arrangement described above, the latch is preferably provided on the body portion, with the channel being provided on the lid portion.

In order to facilitate the breaking of the container following use, the structure of the container preferably comprises a weakened section adapted to be easily broken, so as to enable retrieval of a medical accessory therewithin. Preferably, the weakened section of the container is located adjacent the closure mechanism. More preferably, the weakened section is located adjacent one of the first and second complementary engagement members. Most preferably, in embodiments having the latch-and-channel arrangement, the weakened section is located adjacent the channel.

The container of the present invention preferably further comprises a manually graspable tab associated with the closure mechanism, which tab is adapted such that, when the closure mechanism is closed, pulling of the tab promotes breaking of the weakened section in preference to re-opening of the closure mechanism. The manually graspable tab is preferably associated with one of the first and second complementary engagement members. Most preferably, in embodiments having the latch-and-channel arrangement, the manually graspable tab is associated with the channel.

In view of its intended use in an AER machine, the container of the present invention preferably has a structure adapted to permit the flow of water, or other cleaning fluids, therethrough. This may conveniently be achieved by forming the container with a basket structure. The container is preferably formed by an injection moulding process, from polypropylene or polyethylene, though other suitable plastics materials may be used.

In order to enable the valves to be retained with the particular endoscope to which they are specific, the container preferably further comprises a clip element to enable it to be secured to said endoscope during processing thereof. Means for indicating the identity of the component housed therewithin are preferably also provided on the container. Most preferably, a panel is provided on the container, onto which an identification number of the specific endoscope can be written in indelible ink.

In order that the present invention may be fully understood, a preferred embodiment thereof will now be described in detail, though only by way of example, with reference to the accompanying drawings, in which.

Figure 1:
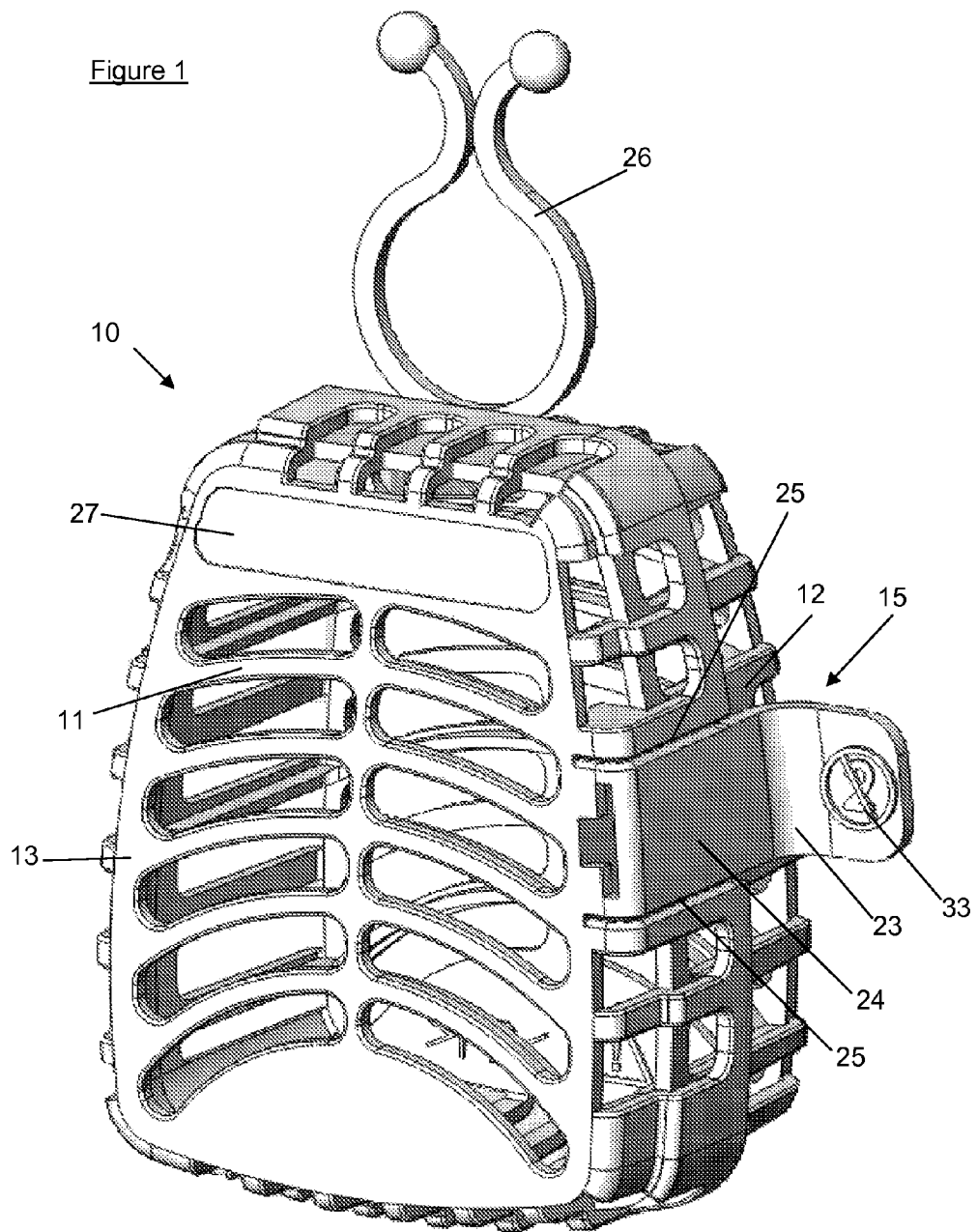
FIG. 1 shows a perspective view of a preferred embodiment of container for housing a medical accessory, according to the present invention, in a closed configuration.

Referring first to FIG. 1, there is shown a preferred embodiment of container, generally indicated 10, for housing a medical accessory—such as a valve 20 (not shown in FIG. 1) of a flexible medical endoscope—during processing thereof. As can be seen, the container 10 is formed with a basket structure 11, so as to permit the flow of water, and cleaning and disinfecting fluids, therethrough during processing.

Figure 2:
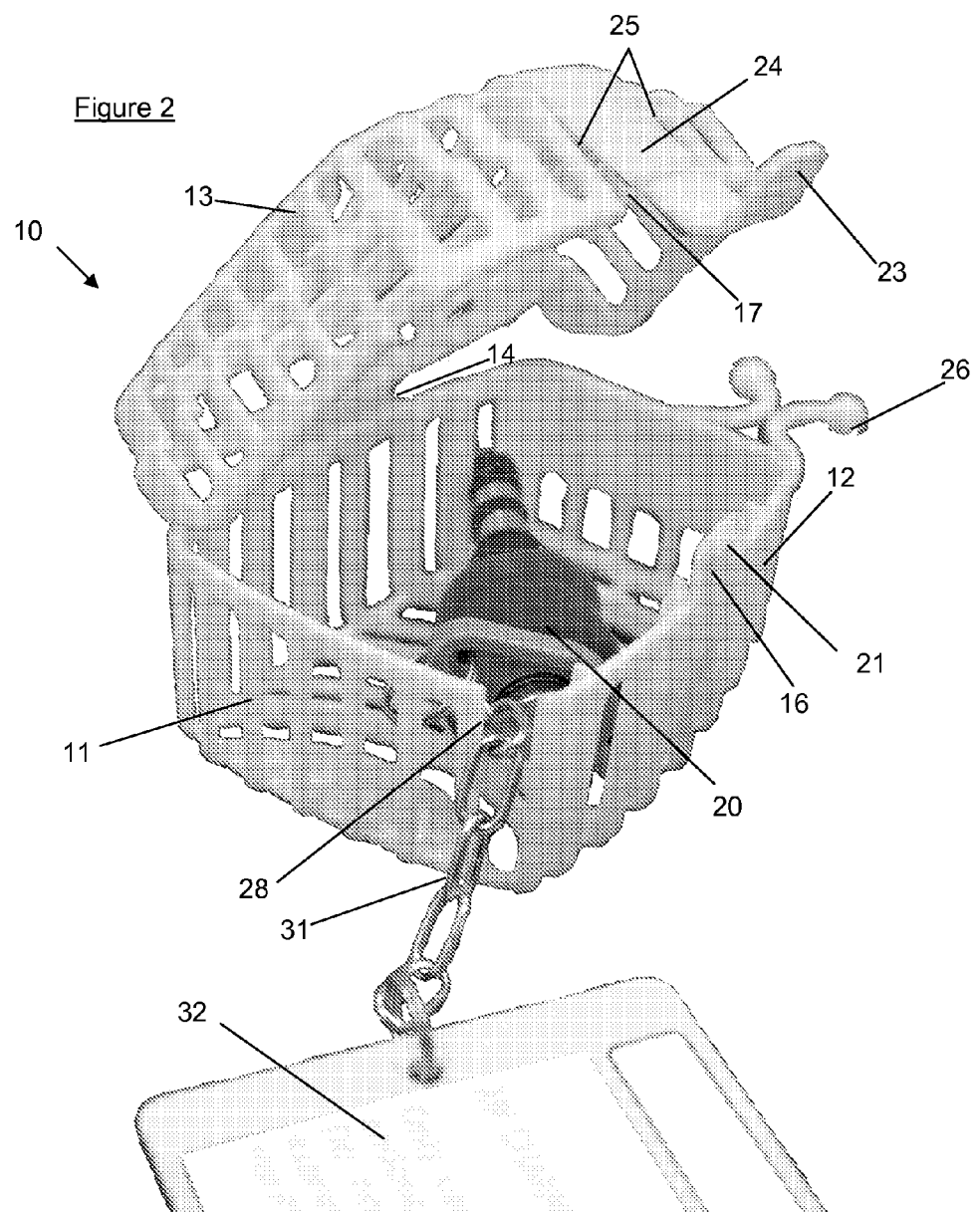
FIG. 2 shows a perspective view of the container of FIG. 1, in an open configuration, and having a valve of flexible medical endoscope therewithin.

As can perhaps best be seen from FIG. 2, the container 10 is formed with a body portion 12 and a lid portion 13. The container 10 is formed from plastics material (polypropylene or polyethylene) by an injection moulding process. This enables the body portion 12 and lid portion 13 to be formed as a single piece of said plastics material, and so to be connected via a live hinge 14—i.e. an especially thin section of said plastics material.

Figure 3:
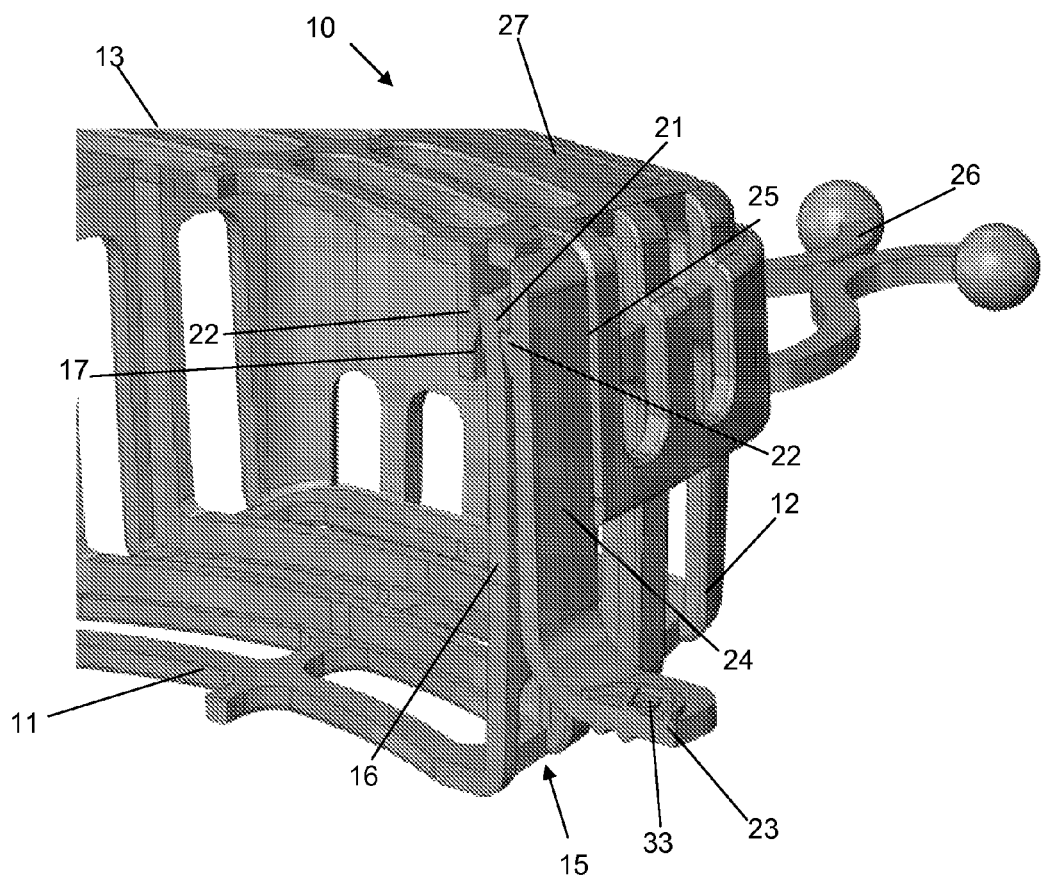
FIG. 3 shows a cross-sectional view through the closure mechanism of the container of FIGS. 1 and 2.

The container 10 is provided with a closure mechanism, generally indicated 15, which is shown in more detail in FIG. 3. The closure mechanism 15 comprises a latch 16 formed on the body portion 12, and a complementary channel 17 formed on the lid portion 13, and adapted to receive said latch 16. As can best be seen in FIG. 3, the latch 16 is provided with an angled barb 21, whilst the channel 17 is provided with detents 22 adapted to engage with the barb 21, thereby to prevent removal of the latch 16 from the channel 17.

Referring again to FIG. 1, it can be seen that the lid portion 13 of the container 10 is provided with a manually graspable tab 23 associated with an external wall 24 of the channel 17. Weakened sections 25 are formed in the structure of the container 10, located either side of the portion of said tab 23 forming the external wall 24 of the channel 17. The weakened sections 25 are formed by providing especially thin sections of plastics material at these locations, and are engineered such that the force required to break said weakened sections 25 is significantly less than the force required to remove the latch 16 from the channel 17 once the barb 21 is engaged with the detents 22.

With the container 10 in its closed configuration with the latch 16 engaged in the channel 17, as shown in FIG. 3, pulling the manually graspable tab 23 thus results in the structure of the container 10 breaking along the weakened sections 25 to open the container 10, rather than disengaging the latch 16 from the channel 17. This ensures that the container 10 cannot be used more than once.

Referring again to FIG. 1, it can be seen that the container 10 is further provided with a clip 26. This enables the container 10 to be clipped onto the tubing of the specific endoscope from which the valve 20 contained therewithin has been removed. The valve 20 can thus remain in close association with its specific endoscope both before, during and after processing, to minimise the risk of cross-contamination by placing the valve 20 of one endoscope into another. To further minimise this risk, the container 10 is further provided with a panel 27 onto which can be written, in water-proof ink, the identification number of the specific endoscope with which the valve 20 is associated.

A further means for minimising the risk of cross-contamination by ensuring the valve 20 remains with a specific endoscope is visible in FIG. 2, and takes the form of a cut-out section 28 in the structure of the container 10. This cut-out section 28 is accessible when the container is in its open configuration as shown in FIG. 2, and is adapted to receive a chain 31 by means of which an identification tag 31 is attached to the valve 20.

A further visual reminder of the single use nature of the container 10 of the present invention can be seen in FIG. 1, and takes the form of a sign 33 provided on the manually graspable tab 23, which sign 33 indicates that the container should not be used a second time.

In use, a valve 20 is removed from an endoscope following use on a patient, and manually cleaned before being placed into the body portion 12 of a container 10 in its open configuration as shown in FIG. 2. The identification tag 32 of the valve remains externally of the container 10, with the connecting chain 31 being placed in the cut-out section 28 of the container 10. The container 10 is then brought into its closed configuration, as shown in FIG. 1, by bringing the lid portion 13 down, rotating it about the live hinge 14, and pressing the lid portion 13 and body portion 12 together such that the closure mechanism 15 engages, with the latch 16 located in the channel 17, as shown in FIG. 3. The container 10 is now securely closed, as the barb 21 engages with the detents 22, so as to prevent the latch 16 being removed from the channel 17, and so prevent the closure mechanism 15 from being opened.

The identification number of the specific endoscope with which the valve 20 is associated is then written on the panel 27, and the container 10 attached to its specific endoscope by means of the clip 26. The endoscope, and its associated valve 20 in its container 10, are then processed and stored together after processing.

When the endoscope is to be used for a subsequent procedure, the container 10 is removed from the endoscope by disengaging the clip 26. The container 10 is then opened by pulling the manually graspable tab 23. This causes the structure of the container 10 to break along the weakened sections 25, in preference to re-opening of the closure mechanism 15, allowing the container 10 to be opened, and the valve 20 removed for re-insertion in its specific endoscope. The container 10 breaks along the weakened sections 25 such that the closure mechanism 15 remains engaged with the latch 16 still securely engaged in the channel 17. This ensures that the container 10 cannot be closed again and so cannot be re-used. The container 10 is thus discarded and a fresh container 10 used for the next processing sequence.

The invention claimed is:

1. A container for housing a medical accessory during processing thereof, said container having
a closure mechanism comprising first and second complementary members adapted to engage with one another such that, once engaged, said first and second complementary members cannot be disengaged without the container breaking, thereby rendering said container suitable only for single use, wherein one of said first and second members comprises a latch provided with an extended barb, and the other of said members comprises a channel adapted to receive said latch and to permit the ingress of said barb, but to prevent removal thereof; and
a clip element to enable said container to be secured to an article of medical equipment during processing thereof.

2. The container as claimed in claim 1, wherein said channel comprises one or more detents adapted to engage with said barb, thereby to prevent removal of the barb from the channel.

3. The container as claimed in claim 1, wherein said barb is angled relative to said latch.

4. The container as claimed in claim 1, having a body portion and a lid portion, and wherein one of said first and second complementary members is provided on said body portion, and the other of first and second complementary members is provided on said lid portion.

5. The container as claimed in claim 1, having a body portion and a lid portion, wherein the latch is provided on the body portion and the channel is provided on the lid portion.

6. The container as claimed in claim 4, wherein said lid portion is hingedly mounted on said body portion.

7. The container as claimed in claim 6, wherein the lid portion and the body portion are formed as a single piece of plastics material, and are connected via a live hinge.

8. The container as claimed in claim 4, wherein said lid portion is shaped so as to engage with said body portion, upon closure of said container.

9. The container as claimed in claim 1, wherein the structure of said container comprises a weakened section adapted to be easily broken following use of said container, so as to retrieve said medical accessory.

10. The container as claimed in claim 9, wherein the weakened section of the container is located adjacent the closure mechanism.

11. The container as claimed in claim 10, wherein the weakened section is located adjacent one of the first and second complementary engagement members.

12. The container as claimed in claim 1, wherein the structure of said container comprises a weakened section adapted to be easily broken following use of said container, and wherein the weakened section is located adjacent the channel.

13. The container as claimed in claim 9, further comprising a manually graspable tab associated with the closure mechanism, said tab being adapted such that, when the closure mechanism is closed, pulling of said tab promotes breaking of said weakened section in preference to re-opening of the closure mechanism.

14. The container as claimed in claim 11, further comprising a manually graspable tab associated with the closure mechanism, said tab being adapted such that, when the closure mechanism is closed, pulling of said tab promotes breaking of said weakened section in preference to re-opening of the closure mechanism, and wherein the manually graspable tab is associated with one of the first and second complementary engagement members.

15. The container as claimed in claim 12, further comprises a manually graspable tab associated with the closure mechanism, said tab being adapted such that, when the closure mechanism is closed, pulling of said tab promotes breaking of said weakened section in preference to re-opening of the closure mechanism, and wherein the manually graspable tab is associated with the channel.

16. The container as claimed in claim 1, having a structure adapted to permit the flow of water, or other cleaning fluids, therethrough.

17. The container as claimed in claim 16, having a basket structure.

* * * * *